United States Patent [19]

El-Chahawi

[11] Patent Number: 4,515,984
[45] Date of Patent: May 7, 1985

[54] PROCESS FOR THE PREPARATION OF ALKALI-METAL FORMYL ACID ESTERS

[75] Inventor: Moustafa El-Chahawi, Troisdorf, Fed. Rep. of Germany

[73] Assignee: Dynamit Nobel Aktiengesellschaft, Troisdorf, Fed. Rep. of Germany

[21] Appl. No.: 419,898

[22] Filed: Sep. 20, 1982

Related U.S. Application Data

[63] Continuation of Ser. No. 217,597, Dec. 18, 1980.

[30] Foreign Application Priority Data

Dec. 22, 1979 [DE] Fed. Rep. of Germany ....... 2952070

[51] Int. Cl.$^3$ ............................................. C07C 67/36
[52] U.S. Cl. .................................... 560/183; 560/177
[58] Field of Search ................. 560/183, 175, 177; 562/517, 518, 519, 577

[56] References Cited

U.S. PATENT DOCUMENTS 2,208,355  7/1940  Beer et al. .......................... 560/183
2,394,255  2/1946  Northey ............................. 560/183

FOREIGN PATENT DOCUMENTS 1047408  6/1965  United Kingdom ................ 560/232

OTHER PUBLICATIONS

Kirk–Othmer *Encyclopedia of Chemical Technology* 2nd Ed. (1964), Interscience Publ. vol. 4, p. 434.
Noller, Carl R. *Chemistry of Organic Compounds* 2nd Ed. (1957), W. B. Saunders, Publ. pp. 814–815.

*Primary Examiner*—Natalie Trousof
*Assistant Examiner*—L. Hendriksen
*Attorney, Agent, or Firm*—Sprung, Horn, Kramer & Woods

[57] ABSTRACT

A process is described for the preparation of an alkali metal formyl acetic acid alkyl ester by reaction of acetic acid alkyl ester, an alkali-metal alcoholate and carbon monoxide at elevated pressure and elevated temperature, the improvement wherein an excess of acetic acid alkyl ester referred to the alkali-metal alcoholate is employed and the reaction is carried out in the absence of a solvent.

11 Claims, No Drawings

PROCESS FOR THE PREPARATION OF ALKALI-METAL FORMYL ACID ESTERS

This is a continuation of application Ser. No. 217,597, filed Dec. 18, 1980.

BACKGROUND OF THE INVENTION

1. Field of the Invention

The invention relates to an improved process for the preparation of alkali-metal formyl acetic acid esters from acetic acid esters, alkali-metal alcoholate and carbon monoxide which employs elevated temperature and elevated pressure.

2. Discussion of Prior Art

From U.S. Pat. No. 2,394,255 it is known to react acetic acid esters with alkali-metal alcoholate e.g. sodium alcoholate in the presence of alkyl formate or carbon monoxide, or preferably alkyl formate and carbon monoxide. There an excess of sodium alcoholate with respect to acetic acid ester is used, and alkyl formate or methanol, which in the presence of carbon monoxide forms alkyl formate, are also present.

The reaction product is a slurry, in other words a suspension of solids in excess alkyl formate and alkali-metal alcoholate, which is difficult to work up to give sodium formyl acetic ester. According to U.S. Pat. No. 2,394,255, the slurry is therefore reacted to give a secondary product. Yield and purity thus are unsatisfactory, and the alkyl formate and sodium alcoholate losses are substantial.

In accordance with German No. 708,513, sodium ethylate and ethyl acetate in a mol ratio of 1:1 are reacted with carbon monoxide in the presence of large amounts of alcohol as solvent. A yield of 85% of a substance of unspecified purity which is convertible to oxymethylene acetic acid ethyl ester only to the extent of 17% is obtained.

SUMMARY OF THE INVENTION

It has now been found that high yields and purities of alkali-metal formyl acetic acid alkyl esters are obtained when only acetic acid alkyl ester, alkali-metal alcoholate and carbon monoxide are present as reactants. The prior formation and utilization of alkyl formate can be dispensed with. The acetic ester should be present in an excess with respect to the alkali-metal alcoholate.

The invention thus has as its object a process for the preparation of an alkali-metal formyl acetic acid alkyl ester by the reaction of an acetic acid alkyl ester with alkali-metal alcoholate and carbon monoxide at elevated pressure and elevated temperature which is characterized in that an excess of acetic acid alkyl ester, referred to the alkali-metal alcoholate, is reacted in the absence of a solvent.

An essential condition is that an excess of acetic ester with respect to alkali-metal alcoholate be used. At least 1.2 mols of acetic ester per mol of alkali-metal alcoholate, and preferably from 2 to 4 mols of acetic ester per mol of alkali-metal alcoholate, should be used. However, an excess of acetic ester of up to 6 mols, and even more if desired, can be used.

Carbon monoxide should be used in amounts of at least 1 mol per mol of alkali-metal alcoholate. The carbon monoxide can contain inert gases such as nitrogen or hydrogen during the reaction. These inert gases can be present in the gas stream in an amount of up to 50 volume percent, preferably 1 to 25 volume percent. The reaction pressure should range from 1 to 100 bars, and preferably from 10 to 50 bars. The reaction temperature can range from 10° to 100° C., and preferably from 30° to 80° C.

Under these conditions, the reaction can go to completion in one hour or less and give yields of 90 weight percent and better.

The acetic ester used is most preferably acetic acid ethyl ester, and optionally acetic acid methyl ester. Preferably the ester function is an alkyl group, e.g. $C_1$-$C_8$ alkyl.

Highly preferred as alkali-metal alcoholate is sodium ethylate. However, sodium methylate and potassium ethylate or potassium methylate can also be used. Generally the alcohol of the alcoholate can be a $C_1$-$C_8$ alkanol although other alcohols, especially aliphatic alcohols can be employed, but only technically produced alcoholates, as ethylates and methylates are reasonably used for technical purposes.

The alkali-metal alcoholate used can range from the 85% grade to the 97% grade, i.e. a 85 to 97 wt % solution of alkali-metal alcoholate in the corresponding alcohol, from which the alcoholate residue has been formed, preferably the 95% technical grade, which has a slight excess of alkali, is used.

It has proved highly advantageous to be able to obtain sodium formyl acetic ester by crystallization from the reaction mixture as a pure substance which is readily separated from excess acetic acid by filtration. Any adhering acetic acid ester can easily be removed in vacuum or by raising the temperature. The excess acetic acid ester is added to the next batch so that there is practically no loss of substance, nor are there any waste products to be removed.

It has been found that the absence of solvents, in accordance with the invention, considerably facilitates the recycling of the excess acetic ester and its reaction. It is surprising that the reaction can be carried out in the absence of the large amounts of solvents used in the prior art and goes to completion in a short time with high yields.

It is also surprising that the reaction can be carried out in the absence of alcohol in free form since it was to be expected that under these conditions acetic ester would react with sodium alcoholate to give acetoacetic ester in accordance with the well-known Claisen condensation.

The substances so prepared find use as intermediate products in the pharmaceutical industry, for example.

EXAMPLE 1

Into a 250-liter pressure vessel equipped with an agitator and a gas inlet pipe, 37 kg (514 mols) 95 wt. % sodium ethylate and 154 kg (1759 mols) acetic acid ethyl ester were introduced under a nitrogen atmosphere. The vessel was then scavenged with carbon monoxide. Carbon monoxide was added with agitation until the pressure reached 20 bars, and the temperature was then raised to 80° C. Heating resulted in a pronounced uptake of carbon monoxide. The pressure was maintained at 20 bars by adding more carbon monoxide. The reaction was completed after 1 hour. The autoclave was cooled and freed of excess carbon monoxide. After scavenging with nitrogen, the solid product was separated by means of a centrifuge. 72.5 kg of sodium formyl acetic acid ethyl ester was obtained. After the separation of adhering acetic ester, 64 kg remained. The yield was 90%.

Conversion to semicarbazone showed that the sodium formyl acetic ester had a purity of over 95%.

EXAMPLE 2

A small amount of fresh acetic ester was added to the filtrate obtained, which was then mixed with sodium ethylate and carbon monoxide as in Example 1. The reaction was completed in 35 minutes and gave the same yield and purity as in Example 1.

What is claimed is:

1. In a process for the preparation of an alkali metal formyl acetic acid alkyl ester by reaction of acetic acid alkyl ester, an alkali-metal alcoholate and carbon monoxide at elevated pressure, the improvement wherein at least 1.2 mols of acetic acid alkyl ester per mol of alkali metal alcoholate is employed, the reaction mixture consists essentially of said acetic acid alkyl ester, alkali metal alcoholate and carbon monoxide, the reaction is conducted at a temperature of 10° to 100° C. and the reaction is carried out in the absence of a substantial amount of added solvent.

2. A process according to claim 1, wherein the reaction mixture consists of said acetic acid alkyl ester, said alkali-metal alcoholate and said carbon monoxide.

3. A process according to claim 1, wherein up to 6 mols of acetic acid ester are employed per mol of alkali-metal alcoholate.

4. A process according to claim 3, wherein 2 to 4 mols of acetic acid ester are employed per mol of alkali-metal alcoholate.

5. A process according to claim 1, wherein the alkali-metal alcoholate is a sodium alcoholate.

6. A process according to claim 5, wherein said alcoholate is sodium methylate or sodium ethylate.

7. A process according to claim 1, wherein said alkali-metal alcoholate is potassium alcoholate.

8. A process according to claim 7, wherein said alcoholate is potassium ethylate or potassium methylate.

9. A process according to claim 1, wherein the process is carried out at a pressure of from 1 to 100 bars.

10. A process according to claim 1, wherein the reaction is carried out with a gas mixture containing carbon monoxide.

11. A process according to claim 1, wherein the process is carried out with a gas mixture containing carbon monoxide and an inert gas.

* * * * *